United States Patent [19]

Zipplies et al.

[11] Patent Number: 5,068,246

[45] Date of Patent: * Nov. 26, 1991

[54] FUNGICIDAL N-SUBSTITUTED 3-ALKYL-4-ARYLPYRROLIDINE DERIVATIVES

[75] Inventors: Matthias Zipplies, Hirschberg; Hubert Sauter, Mannheim; Walter Himmele, Walldorf; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[*] Notice: The portion of the term of this patent subsequent to Nov. 26, 2008 has been disclaimed.

[21] Appl. No.: 251,252

[22] Filed: Sep. 30, 1988

[30] Foreign Application Priority Data

Sep. 30, 1987 [DE] Fed. Rep. of Germany ....... 3732910

[51] Int. Cl.$^5$ ..................... A01N 43/36; A01N 43/08; A01N 43/28; C07D 207/06
[52] U.S. Cl. ...................... 514/429; 514/63; 514/409; 514/422; 514/428; 548/406; 548/407; 548/517; 548/527; 548/570; 548/575; 548/577
[58] Field of Search .............. 548/406, 570, 575, 577, 548/407, 517, 527; 514/63, 428, 429, 409, 422

[56] References Cited

U.S. PATENT DOCUMENTS 4,301,281 11/1981 Buschmann et al. ............... 544/106
4,472,412 9/1984 Buschmann et al. ............ 548/578 X

FOREIGN PATENT DOCUMENTS 0000333 1/1979 European Pat. Off. .
0182224 5/1986 European Pat. Off. .
0243940 11/1987 European Pat. Off. .
0244739 11/1987 European Pat. Off. .
2727482 1/1979 Fed. Rep. of Germany .

Primary Examiner—Joseph Paul Brust
Attorney, Agent, or Firm—Oblon, Spivak, McClelland, Maier & Neustadt

[57] ABSTRACT

3-Alkyl-4-arylpyrrolidine derivatives of the formula

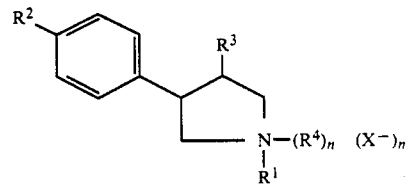

where
$R^1$ is alkenyl, alkynyl, cycloalkyl, cycloalkenyl, alkyl-cycloalkyl, cycloalkyl-alkyl, alkyl-cycloalkyl-alkyl, cycloalkenyl-alkyl, alkyl-cycloalkenyl, bicycloalkyl, bicycloalkylalkyl, alkyl-bicycloalkyl, heterocycloalkyl, heterocycloalkylmethyl, aryl, arylalkyl, alkylary, alkyl-aryl-alkyl,
$R^2$ is alkyl, alkoxy,
$R^3$ is alkyl
$R^4$ is alkyl, alkenyl, alkynyl and phenylalkyl,
$X^-$ is a plant-tolerated anion, and
n is 0 or 1, their plant-tolerated salts, and fungicides containing these compounds.

6 Claims, No Drawings

FUNGICIDAL N-SUBSTITUTED 3-ALKYL-4-ARYLPYRROLIDINE DERIVATIVES

BACKGROUND OF THE INVENTION

1. Field of the Invention

The present invention relates to novel N-substituted 3-alkyl-4-arylpyrrolidines, processes for their preparation, their use as fugnicides, fungicides which contain the novel active ingredients, processes for the preparation of such fungicides and methods for controlling fungi with these active ingredients.

2. Discussion of the Background

DE 2 727 482 discloses an arylalkylpyrrolidine derivative of the formula below as a compound having a fungicidal action.

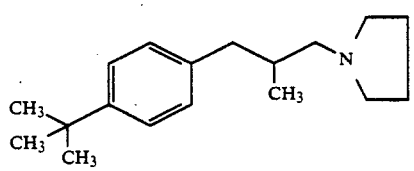

However, its fungicidal action is unsatisfactory.

SUMMARY OF THE INVENTION

We have found that compounds of the formula I

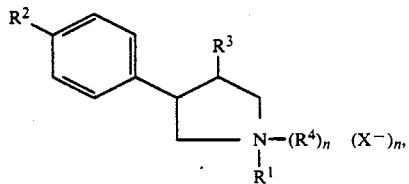

where $R^1$ is $C_2$–$C_{20}$-alkyl which is unsubstituted or substituted by hydroxyl, halogen, $C_1$–$C_5$-alkoxy or $C_3$–$C_9$-trialkylsilyl, $C_3$–$C_{20}$-alkenyl, $C_3$–$C_{20}$-alkynyl, unsubstituted or substituted $C_4$–$C_{12}$-cycloalkyl, $C_4$–$C_{12}$-cycloalkenyl, unsubstituted or substituted $C_4$–$C_{20}$-alkylcycloalkyl, $C_4$–$C_{20}$-cycloalkylalkyl, $C_4$–$C_{20}$-alkylcycloalkylalkyl, $C_4$–$C_{20}$-cycloalkenylalkyl, unsubstituted or substituted $C_9$–$C_{11}$-bicycloalkyl, $C_{10}$–$C_{15}$-bicycloalkylalkyl, unsubstituted or substituted $C_{10}$–$C_{15}$-alkylbicycloalkyl, 5-membered to 7-membered heterocycloalkyl having one or two hetero atoms from the group consisting of oxygen and/or sulfur, 5-membered to 7-membered heterocycloalkylmethyl having 1 or 2 hetero atoms from the group consisting of oxygen and/or sulfur, $C_1$–$C_8$-alkyl-substituted 5-membered to 7-membered heterocycloaklyl or heterocycloalkylmethyl having 1 or 2 hetero atoms from the group consisting of oxygen and/or sulfur, unsubstituted or substituted aryl, unsubstituted or substituted $C_7$–$C_{20}$-arylalkyl, $C_7$–$C_{20}$-alkylaryl or $C_8$–$C_{20}$-alkylarylalkyl, $R^2$ is $C_3$–$C_{10}$-alkyl or $C_3$–$C_8$-alkoxy, $R^3$ is $C_1$–$C_4$-alkyl, $R^4$ is $C_1$–$C_5$-alkyl, $C_3$–$C_5$-alkenyl, $C_3$–$C_5$-alkynyl or $C_7$- or $C_8$-phenylalkyl, $X^-$ is an anion tolerated by plants and n is 0 or 1, and their plant-tolerated salts have excellent fungicidal activity coupled with good toleration by plants.

Salts are understood as salts with plant-tolerated anions $X^-$ of any inorganic and organic acids, e.g. hydrochloric acid, hydrofluoric acid, hydriodic acid, hydrobromic acid, sulfuric acid, phosphoric acid, dodecylbenzenesulfonic acid, $C_1$–$C_{16}$-alkylcarboxylic acids, formic acid, acetic acid, propionic acid, palmitic acid, perfluoroheptanoic acid, oxalic acid, malonic acid, benzoic acid, malic acid, dodecylsulfuric acid, glycerol-2-phosphoric acid, methylsulfuric acid, methanesulfonic acid, p-toluenesulfonic acid or nitric acid, and salts such as bisulfates or dihydrogen phosphates.

DETAILED DESCRIPTION OF THE PREFERRED EMBODIMENTS

The novel N-substituted 3-alkyl-4-arylpyrrolidines of the formula I and their salts contain chiral centers. They are obtained in general as racemates or may be obtained as diastereomer mixtures. Some of the novel compounds can be isolated in pure diastereomeric form, for example by distillation, column chromatography or on the basis of solubility differences. Pure enantiomeric compounds can be obtained, for example, by resolution of the racemate with a chiral auxiliary reagent by a known method, for example via diastereomeric salts. Regarding the use of the novel N-substituted 3-alkyl-4-arylpyrrolidines as fungicides, the diastereomers and the enantiomers as well as their stereoisomer mixtures obtained in the synthesis are suitable. They all form a subject of the invention.

$R^1$ is, for example, straight-chain or branched $C_2$–$C_{20}$-alkyl, in particular $C_3$–$C_{19}$-alkyl, e.g. propyl, isopropyl, butyl, isobutyl, but-2-yl, tert-butyl, pentyl, pent-2-yl, pent-3-yl, 1,2-dimethylpropyl, 2,2-dimethylpropyl, hexyl, hex-2-yl, hex-3-yl, 2,3,3-trimethylbut-2-yl, 1,4-dimethylpentyl, 4-methylpent-2-yl, 4-methylpentyl, 3,3-dimethylbutyl, heptyl, hept-2-yl, hept-3-yl, hept-4-yl, diisopropylmethyl, 1,4-dimethylpentyl, 4,4-dimethylpentyl, octyl, 2-methylhept-3-yl, 5-methylhept-3-yl, oct-2-yl, oct-3-yl, oct-4-yl, 5,5-dimethylhexyl, 2,4,4-trimethylpentyl, 6-methylhept-2-yl, nonyl, non-2-yl, non-3-yl, non-4-yl, non-5-yl, 2,5,5-trimethylhexyl, 2,6-dimethylhept-4-yl, 3,5,5-trimethylhexyl, decyl, dec-2-yl, dec-3-yl, dec-4-yl, 2,3,5,5-tetramethylhexyl, undecyl, dodecyl, tridecyl, 1,5,9-trimethyldecyl or tetradecyl, $C_2$–$C_{20}$-hydroxyalkyl, in particular $C_2$–$C_8$-hydroxyalkyl, e.g. hydroxyethyl, hydroxypropyl, hyroxy-butyl, hydroxypentyl, hydroxyhexyl, hydroxyheptyl, 1-hydroxybut-2-yl or 2-hydroxybut-3-yl, $C_2$–$C_{20}$-haloalkyl, in particular $C_2$–$C_{10}$-haloalkyl, having 1-3 halogen atoms, such as chlorine, bromine or fluorine, e.g. 3-chloropropyl, 6-chlorohexyl, trifluoroethyl, trichloroethyl, 5-chloro- pent-2-yl, 3-chlorobut-2-yl or 3,3-dichloroprop-2-yl, $C_1$–$C_5$-alkoxy-$C_2$–$C_{20}$-alkyl, in particular $C_1$-$C_4$-alkoxy-$C_2$–$C_{10}$-alkyl, e.g. methoxyethyl, ethoxyethyl, tert-butoxy-ethyl, 3-tert-butoxypropyl, 4-tert-butoxytutyl, methoxypropyl, methoxybutyl, methoxypentyl, methoxyhexyl, ethoxyhexyl or 3-methoxyprop-2-yl, $C_3$–$C_9$-trialkylsilyl-$C_2$–$C_{20}$-alkyl, in particular $C_3$–$C_6$-trialkylsilyl-$C_2$–$C_{10}$-alkyl, e.g. trimethylsilylethyl, trimethylsilylpropyl, trimethylsilylbutyl, trimethylsilylpentyl or 6-trimethylsilylhexyl, $C_3$–$C_{20}$-alkenyl, in particular $C_3$–$C_{14}$-alkenyl, e.g. allyl, methallyl, dimethylallyl, hexenyl or 1,5,9-trimethyldecadienyl, $C_3$–$C_{20}$-alkynyl, in particular $C_3$–$C_6$-alkynyl, e.g. propargyl or 4,4-dimethyl-2-butyn-1-yl, $C_4$–$C_{12}$-cycloalkyl, e.g. cyclobutyl, cyclopentyl, cyclohexyl, cycloheptyl or cyclododecyl, $C_4$–$C_{12}$-hydroxycycloaklyl, e.g. 4-hydroxycyclohexyl, $C_1$–$C_5$-alkoxy-$C_4$–$C_{12}$-cycloalkyl, e.g. 4-methoxycyclohexyl or 4-tert-butoxycyclohexyl, $C_3$–$C_9$-trialkylsylyl-$C_4$–$C_{12}$-cycloalkyl, e.g. 4-trimethylsilylcyclohexyl, $C_4$–$C_{12}$- cycloalkenyl, e.g. cyclopentenyl, cyclohexenyl or cycloheptenyl, $C_4$–$C_{20}$-alkylcycloalkyl, such as $C_1$–$C_8$-alkyl-$C_4$–$C_8$-cycloalkyl, e.g. 4-methylcyclohexyl, 3-methylcyclohexyl, 3,3-dimethylcyclohexyl, 3,3,5-trimethylcyclohexyl, 4-isopropylcyclohexyl, 4-tert-butylcyclohexyl, 4-(2-methylbut-2-yl)-cyclohexyl or 4-(2,4,4-trimethylpent-2-yl)-cyclohexyl, $C_4$–$C_{10}$-alkylhydroxycycloalkyl, such as $C_1$–$C_4$-alkylhydroxy-$C_4$–$C_8$-cycloalkyl, e.g. 4-hydroxy-3,6-dimethylcyclohhexyl, 4-hydroxy-3,3-dimethylcyclohexyl or 4-hydroxy-3,3,5-trimethylcyclohexyl, $C_5$–$C_{20}$-cycloalkylalkyl, such as $C_4$–$C_8$-cycloalkyl-$C_1$–$C_4$-alkyl, e.g. cyclohexylmethyl, cyclohexylethyl or cyclohexylpropyl, $C_4$–$C_{20}$-alkylcycloalkenyl, e.g. 4-isopropylcyclohexenyl or 4-tert-butylcyclohexenyl, $C_9$–$C_{11}$-bicycloalkyl, e.g. [4.3.0]bicyclononyl or decalyl, $C_9$–$C_{11}$-hydroxybicycloalkyl, e.g. 6-hydroxy-2-decalyl or 7-hydroxy-2-decalyl, $C_{10}$–$C_{15}$-alkylbicycloalkyl, e.g. 9-methyl-2-decalyl, 5,9-dimethyl-2-decalyl or 5,5,9-trimethyl-2-decalyl, $C_{10}$–$C_{15}$-alkylhydroxybicycloalkyl, e.g. 6-hydroxy-9-methyl-2-decalyl, 6-hydroxy-5,9-dimethyl-2-decalyl or 6-hydroxy-5,5,9-trimethyl-2-decalyl, 5membered to 7-membered heterocycloalkyl having 1 or 2 hetero atoms from the group consisting of oxygen and sulfur, e.g. tetrahydropyranyl, tetrahydrothiopyranyl or dioxanyl, 5-membered to 7-membered heterocycloalkylmethyl having 1 or 2 hetero atoms from the group consisting of oxygen and sulfur, e.g. tetrahydropyranylmethyl or dioxanylmethyl, $C_1$–$C_8$-alkyl-substituted 5-membered to 7-membered heterocycloalkyl or heterocycloalkylmethyl having 1 or 2 hetero atoms from the group consisting of oxygen and sulfur, e.g. 3,5-diethyldioxan-2-ylmethyl, 3,6-diethyldioxan-2-ylmethyl or 3,5-dimethyldioxan-2-ylmethyl, aryl which is unsubstituted or substituted by hydroxyl, 1–3 halogen atoms, such as chlorine, bromine or fluorine, $C_2$–$C_5$-alkoxy or $C_3$–$C_9$-trialkylsilyl, e.g. phenyl, 4-hydroxyphenyl, 4-chlorophenyl, 2,4-dichlorophenyl, 4-tert-butoxyphenyl or 4-trimethylsilylphenyl, $C_7$–$C_{20}$-arylalkyl which is unsubstituted or substituted by hydroxyl, 1–3 halogen atoms, such as chlorine, bromine or fluorine, $C_1$–$C_5$-alkoxy or $C_3$–$C_9$-trialkylsilyl, e.g. benzyl, 4-chlorobenzyl, 2,4-dichlorobenzyl, 4-bromobenzyl, 4-tert-butoxybenzyl, 4-trimethylsilylbenzyl or 4-phenyl-4-methylpentyl, $C_7$–$C_{20}$-alkylaryl, e.g. 4-tert-butylphenyl, or $C_8$–$C_{20}$-alkylarylalkyl, e.g. 4-tert-butylbenzyl, 4-tert-butylphenethyl, 4-tert-butylphenylpropyl or 3-(4-tert-butylphenyl)-2-methylpropyl.

$R^2$ is, for example, branched or straight-chain $C_3$–$C_{10}$-alkyl or $C_3$–$C_8$alkoxy, e.g. propyl, isopropyl, sec-butyl, tert-butyl, 2-methylbut-2-yl, 2,4,4-trimethylpent-2-yl, propoxy, butoxy or tert-butoxy.

$R^3$ is, for example, $C_1$–$C_4$-alkyl, e.g. methyl, ethyl, propyl, isopropyl or butyl, and $R^4$ is, for example, $C_1$–$C_5$-alkyl, e.g. methyl, ethyl or propyl, $C_3$–$C_5$-alkenyl, e.g. allyl or methallyl, $C_3$–$C_5$-alkynyl, e.g. propargyl or butynyl, or $C_7$- or $C_8$-phenylalkyl, e.g. benzyl.

Compounds of the formula I can be prepared, for example, as follows:

By N-alkylation of pyrrolidines

Where $R^2$ is alkyl, by Friedel-Crafts alkylation of N-alkylated phenylpyrrolidines By reactions which synthesize the hetero ring and start from suitable intermediates, followed by reduction.

The processes are described below.

Introduction of the radical $R^1$ a) Reaction of a pyrrolidine derivative II with a compound $R^1$-X under basic conditions.

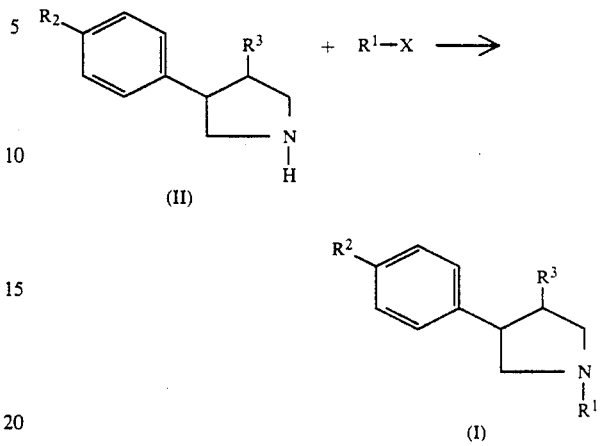

X is, for example, chlorine, bromine, iodine, methanesulfonyl, benzenesulfonyl or p-toluenesulfonyl.

The reaction is carried out at 40°–200° C. in the presence or absence of an inert solvent. Preferred bases are inorganic bases, e.g. potassium hydroxide, sodium hydroxide, lithium hydroxide, sodium hydride, potassium carbonate and sodium carbonate. Organic bases, such as triethylamine, dicyclohexylamine and diisopropylamine, are also suitable. The reaction can also be carried out using an excess of the pyrrolidine derivative II.

b) Reaction of a carbonyl compound III

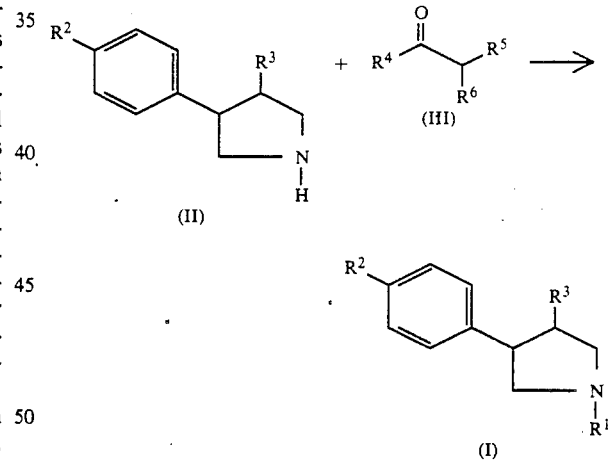

where $R^4$, $R^5$ and $R^6$ are defined such that the radical

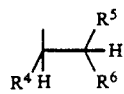

in its entirety corresponds to the radical $R^1$, with a pyrrolidine derivative II with simultaneous or subsequent reduction or hydrogenation.

$b_1$) In the direct method for the preparation of the compound I, a mixture of II and II is reacted in the presence of a solvent, e.g. methanol, ethanol, propanol or isopropanol, which may contain up to 25% by volume of water, with sodium cyanoborohydride or sodium borohydride, in the presence or absence of a metal salt, such as zinc(II) chloride, cadmium(II) chloride or magnesium(II) chloride, at 0°–100° C., preferably 20°–80° C., or in the presence of a solvent, e.g. methanol, ethanol, tetrahydrofuran or toluene, and of a hydrogenation catalyst, e.g. Raney nickel, platinum(IV) oxide, Ru$_2$O$_3$ or palladium on carbon, in an autoclave at 100°–150° C. with hydrogen until the pressure remains constant.

b$_2$) In the two-stage reaction, an enamine is prepared from the compounds II and III in a conventional manner under water-eliminating conditions, and the product is then hydrogenated with hydrogen using a noble metal catalyst, such as Raney nickel, Raney cobalt, PtO$_2$ or Ru$_2$O$_3$, preferably palladium on carbon, or is reduced with formic acid by the Leukart-Wallach method.

c) Where R$^2$ is C$_3$–C$_{10}$-alkyl, R$^2$ can be introduced into a phenylpyrrolidine derivative of the structure IV

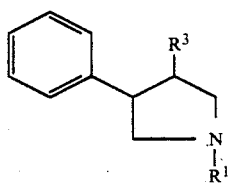

(IV)

by reacting the said derivative under acid catalysis with an alkene of the structure Va

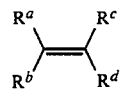

(Va)

where R$^a$ to R$^d$ are defined such that the radical Vb in its entirety

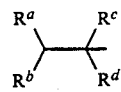

(Vb)

corresponds to the radical R$^2$, or with an alkyl halide R$^2$-X. Mineral acids, e.g. sulfuric acid, hydrochloric acid, HF or hydrobromic acid, or Lewis acids, such as AlCl$_3$ or SnCl$_4$, are used and the reaction is carried out while cooling with ice, for example at from −10° to +20° C.

d) Ring-synthesizing reactions

The compounds I can also be prepared by reacting a primary amine of the formula R$^1$-NH$_2$ with a compound VIa, VIb, VIc or VId and then reducing the carbonyl group or groups.

In the reaction of dicarbonylic acids, succinic anhydrides and lactones having a 5-membered ring, the water of reaction is removed from the equilibrium either in a water separator using a suitable entraining agent or in the presence of a water-binding agent.

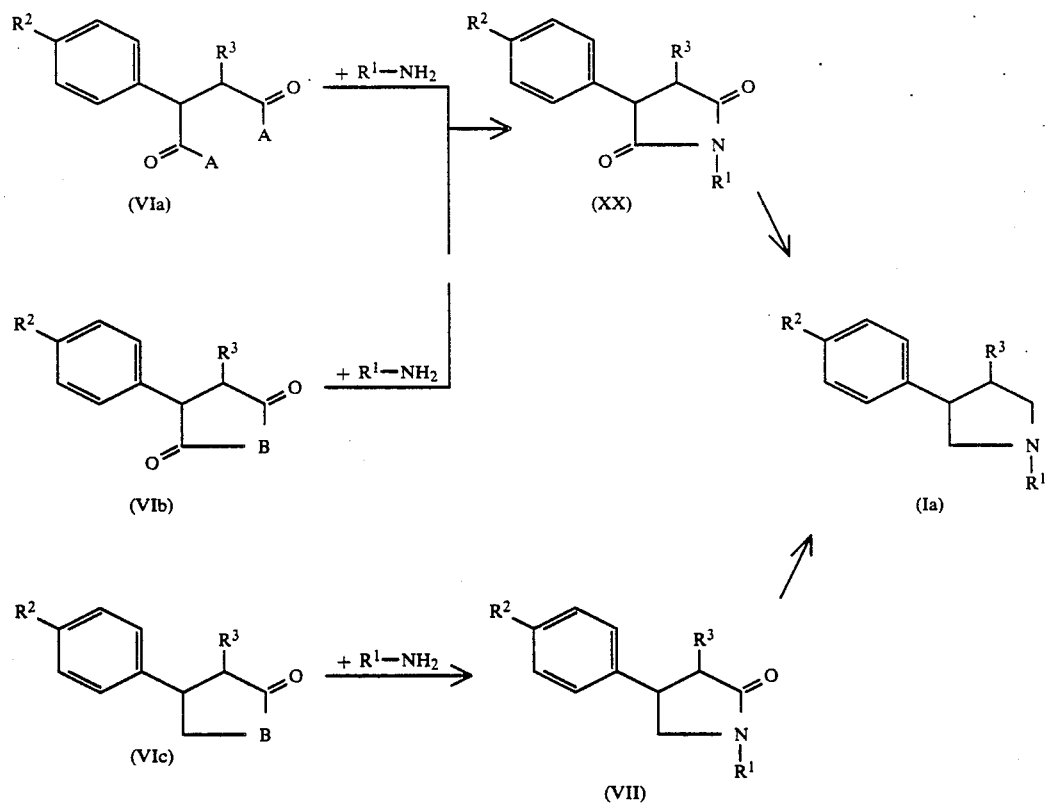

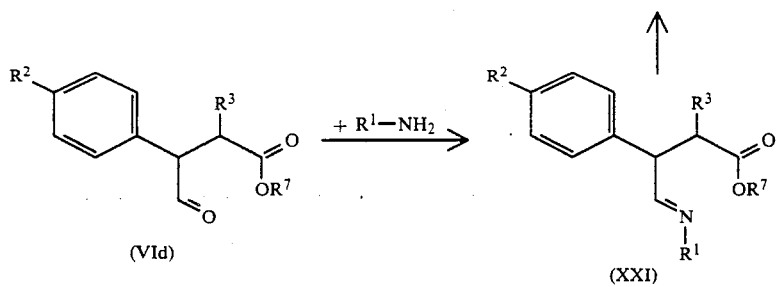

(VId)                                                (XXI)

A = hydroxyl, alkoxy or halogen
B = oxygen or NH
$R^7$ = alkyl

Suitable solvents for the water separation are fairly high boiling hydrocarbons, such as toluene, xylene, chlorobenzene or naphtha. Suitable water-binding agents are acetic anhydride and molecular sieves.

However, it is also possible to dispense with a solvent. The reactions can be carried out at 100° C. or higher. If the reaction temperature cannot be reached under atmospheric pressure, the reaction is carried out in an autoclave under the autogenous pressure of the reaction mixture at the required conversion temperature.

The dicarbonyl dihalides can be reacted at from −20° to +100° C., preferably from 0° C. to −10° C., in the presence of a base which may additionally serve as a solvent, e.g. diisoopropylamine, tributylamine, pyridine, picoline, triethylamine or dicyclohexylamine, or of a base such as sodium carbonate, potassium carbonate or sodium bicarbonate in the presence of an inert solvent, such as chloroform, dichloromethane or tetrahydrofuran.

The reaction of the amine derivatives $R^1$-$NH_2$ with a lactone derivative having a 5-membered ring (VIc, B=NH) takes place more readily at elevated temperatures of from 150° to 280° C., and the required reaction temperature may only be achievable in an autoclave. The reaction can be carried out in an inert solvent, for example toluene, xylene, ethanol, isopropanol or cyclohexanol, or in the absence of a solvent.

The carbonyl compound can be reduced to the alkyl compound by reaction with a reducing agent at from −20° to +100° C., preferably from 0° to +60° C. Preferably used reducing agents are hydrides, such as lithium aluminum hydride or diborane.

The reduction can also be carried out under Wolff-Kishner reaction conditions or electrochemically.

Suitable solvents for the hydride reaction are ethers, such as diethyl ether, diisopropyl ether, methyl tert-butyl ether, tetrahydrofuran or dioxane, and hydrocarbons, such as xylene or toluene.

The 3-formyl-propionate derivatives of the general structure VId can be reacted with the amines $R^1$-$NH_2$ at 0°-100° C. in the presence or absence of a water-eliminating agent, such as sodium sulfate, magnesium sulfate or a molecular sieve, or in a water separator using a suitable entraining agent, to give the Schiff's bases of the general structure X.

Suitable solvents are chlorohydrocarbons, such as dichloromethane, ethers, such as tetrahydrofuran, and hydrocarbons, such as toluene or xylene.

The compounds XXI can be converted into the pyrrolidone derivatives VII using reducing agents, such as sodium borohydride or lithium aluminum hydride, or with hydrogen over catalysts, such as palladium/active carbon or Raney nickel. These pyrrolidone derivatives can be reacted, as described above, with reducing agents, e.g. lithium aluminum hydride, in an ether, such as tetrahydrofuran or dioxane, to give the novel compounds Ia.

The quaternary salts can be prepared from the compound I by reaction with a compound of the formula $R^4$-X, where $R^4$ and X have the abovementioned meanings.

The preparation of pyrrolidines which are unsubstituted at the nitrogen atom can be carried out as described below.

a) Synthesis of 3-alkyl-4-phenylpyrrolidines based on correspondingly substituted cinnamyl alcohols 1. In order to be able to carry out a hydroformylation smoothly, a cinnamyl alcohol of the formula XXII is esterified with acetic anhydride (selectivity >97%).

2. The cinnamyl ester VIII is reacted with CO and hydrogen using a rhodium complex catalyst. The formyl group enters predominantly at the α-position with respect to the aromatic. The hydroformylation product is purified by fractionation (selectivity >90%).

3. The aldehyde ester IX is reacted with ammonia and hydrogen using a cobalt or nickel catalyst. Reaction first takes place at the carbonyl group; subsequently, the acetyl group migrates to the amino group. Predominantly the acetylpyrrolidine derivative XI is isolated. One fraction obtained is the 4-aminobutanol derivative X.

4. To complete cyclization in the 4-aminoalcohol X and simultaneously hydrolyze the acetyl group, the compound is treated with sulfuric acid at 50° C.

5. After the mixture has been rendered alkaline, the 3-alkyl-4-arylpyrrolidine II can be extracted with toluene. Purification is effected by fractionation under reduced pressure (selectivity of stages 3–5 about 60%).

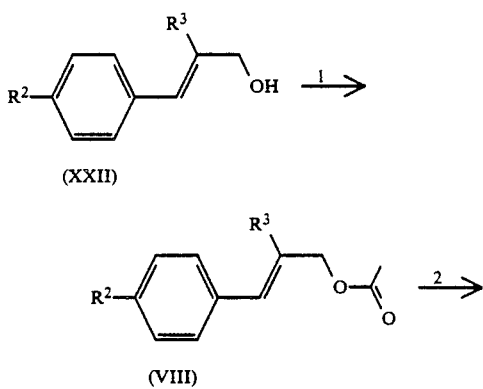

-continued

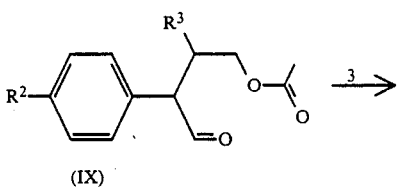
(IX)

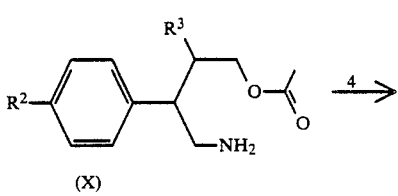
(X)

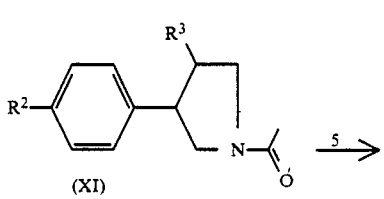
(XI)

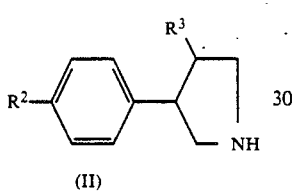
(II)

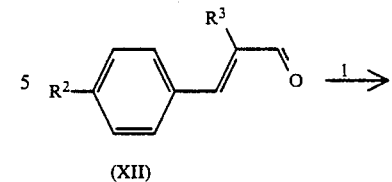
(XII)

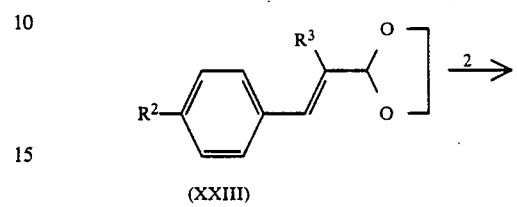
(XXIII)

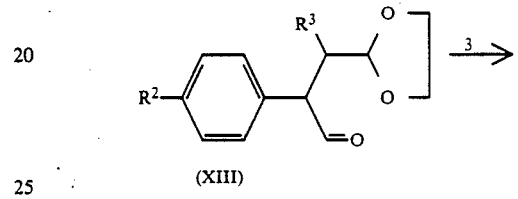
(XIII)

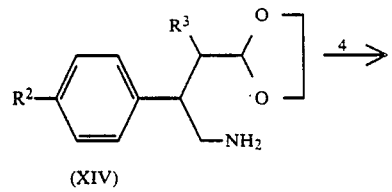
(XIV)

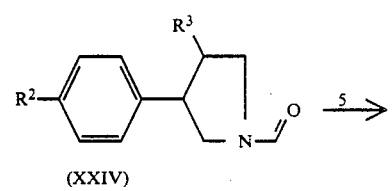
(XXIV)

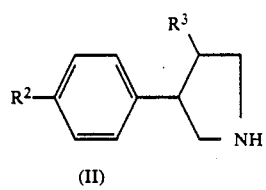
(II)

b) Synthesis of 3-alkyl-4-arylpyrrolidines based on correspondingly substituted cinnamaldehydes 1. The cinnamaldehydes XII are unsaturated carbonyl compounds and cannot be hydroformylated in this form. In order to be able to convert these aldehydes, the conjugation must be eliminated. This can be achieved by conversion into an acetal. The acetalization is advantageously carried out using glycol as an acetalization component, with the aid of a moderately strong acid. (Selectivity when the unconverted cinnamaldehyde is recycled: >85%).

2. The hydroformylaltion of the acetal XXIII can be carried out with a 1:1 CO/H₂ mixture using a rhodium-olefin complex catalyst, at 100° C. and under 650 mbar. The succinaldehyde hemiacetal XIII can be purified by fractionation. (Selectivity >80%).

3. The 4-aminobutanal acetal XIV is synthesized by hydrogenation using a Co or Ni catalyst under aminating conditions. The aminoacetal XIV can likewise be purified by fractional distillation under reduced pressure. (Selectivity >80%).

4. Cyclization to give XXIV with simultaneous reduction is achieved by boiling with formic acid. The selectivity depends to a very great extent on the substituents on the aromatic.

5. The hydrolysis of the amide can advantageously be achieved by boiling with sulfuric acid, liberating the base by rendering the mixture alkaline and extracting with toluene. The 3-alkyl-4-arylpyrrolidine II is purified by fractional distillation.

c) Synthesis of 3-alkyl-4-phenylpyrrolidine based on correspondingly substituted cinnamates 1. A correspondingly substituted cinnamate XV is reacted with CO and H₂ with catalysis with rhodium oxide hydrate under superatmospheric pressure and at elevated temperatures. The corresponding 4-oxobutyrate (VId) is virtually exclusively formed. Purification is effected by fractionation under reduced pressure. The selectivity is about 75%.

2. The oxobutyrate (VId) is converted by hydrogenation in the presence of a Cu or other hydrogenation catalyst into the 4-hyudroxybutyrate XVI. The latter eliminates alcohol during purification by distillation and is converted into the corresponding γ-butyrolactone XVII. (Selectivity of the hydrogenation >90%).

3. The conversion of the lactone XVII into the lactam XVIII is carried out by forcing in aqueous ammonia at 250° C. under nitrogen pressure. The lactam can be purified by fractionation under reduced pressure. (Selectivity >90%).

4. The carbonyl group in XVIII is most readily reducing using lithium aluminum hydride. (Selectivity >90%).

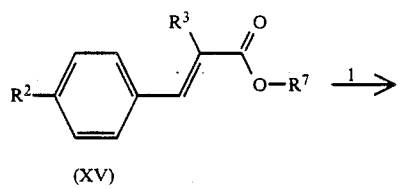

(XV)

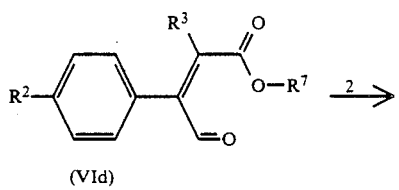

(VId)

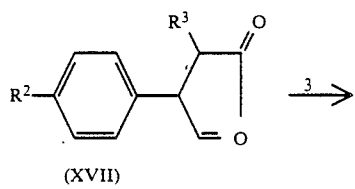

(XVII)

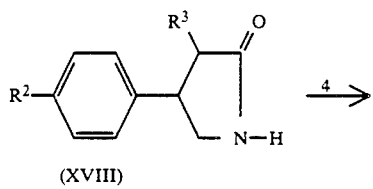

(XVIII)

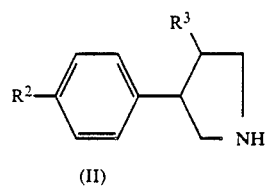

(II)

The Examples which follow illustrate the preparation of the novel compounds.

PREPARATION EXAMPLES

EXAMPLE 1

N-(4-tert-butylcyclohexyl)-3-methyl-4-(4-tert-butylphenyl)-pyrrolidine (compound No. 92)

2.17 g (10 millimoles) of 3-methyl-4-(4-tert-butylphenyl)-pyrrolidine (80% of transisomer), 1.54 g (10 millimoles) of 4-tert-butylcyclohexanone, 0.75 g (5.5 millimoles) of zinc(II) chloride and 0.70 g (11 millimoles) of sodium cyanoborohydride in 100 ml of absolute methanol are stirred for 48 hours at 20° C. The solvent is evaporated under reduced pressure, and the residue is dissolved in 5% strength sodium hydroxide solution and methyl tert-butyl ether. The organic phase is washed with sodium chloride solution and water, dried and evaporated under reduced pressure, and the residue is subjected to incipient distillation under 0.4 bar at up to 140° C. Yield: 1.9 g (54%) of a viscous resin.

EXAMPLE 2

N-(2,3,5,5-tetramethylhexyl)-3-methyl-4-(p-tert-butylphenyl)-pyrrolidine (compound No. 46)

57 g of 2,3,5,5-tetramethylhexanal are added to 72 g of 3-methyl-4-(p-tert-butylphenyl)-pyrrolidine, and the mixture is refluxed using xylene in the course of 6.5 hours, and the water formed is separated off. 4.2 g of water are removed. 16 g of formic acid are added dropwise to the reaction solution, and the stirred mixture is heated at the b oil at from 132° to 142° C. The elimination of $CO_2$ is complete after 4 hours. The reaction product is purified by molecular distillation under 2 mbar. 9.9 g of first runnings are obtained up to a distillation temperature of 168° C. The major amount (93 g) passes over at from 168° to 170° C. The distillation residue comprises 4 g. According to the H-NMR and IR spectra, the 1-(2,3,5,5-tetramethylhexyl)-3-methyl-4-(p-tert-butylphenyl)-pyrrolidine is in the form of an isomer mixture.

EXAMPLE 3

Preparation of 1-methyl-1-(2,3,5,5-tetramethylhexyl)-3-methyl-4-(-p-tert-butylphenyl)-pyrrolidinium bromide (compound No. 189)

30 g of tetrahydrofuran are added to 40 g of 1-(2,3,5,5-tetramethylhexyl)-3-methyl-4-(p-tert-butylphenyl)-pyrrolidine. For the formation of the quaternary salt, 40 g of a solution of methyl bromide in acetonitrile (20% strength) are added. When the mixture stands overnight, the quaternary salt crystallizes out. Filtration with suction gives 20.5 g of product of melting point 250° C. At 270° C., pronounced discoloration occurs.

The compounds below can be prepared in a similar manner.

TABLE 1

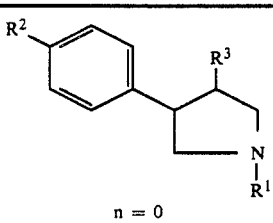

n = 0

| Comp. No. | $R^1$ | $R^2$ | $R^3$ | IR absorption (cm$^{-1}$) [film] |
|---|---|---|---|---|
| 1 | n-propyl | tert.-butyl | methyl | |
| 2 | isopropyl | tert.-butyl | methyl | |

TABLE 1-continued

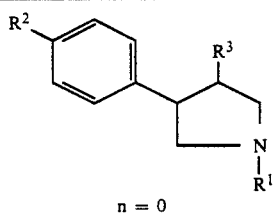

n = 0

| Comp. No. | R¹ | R² | R³ | IR absorption (cm⁻¹) [film] |
|---|---|---|---|---|
| 3 | n-butyl | tert.-butyl | methyl | |
| 4 | isobutyl | tert.-butyl | methyl | |
| 3 | sec.-butyl | tert.-butyl | methyl | |
| 4 | tert.-butyl | tert.-butyl | methyl | |
| 5 | n-pentyl | tert.-butyl | methyl | |
| 6 | 3-methyl-butyl | tert.-butyl | methyl | |
| 7 | 2,2-dimethyl-propyl | tert.-butyl | methyl | oil 2954, 2904, 2868, 2779, 1510, 1478, 1463, 1394, 1361, 1129, 829, 573. |
| 8 | pent-2-yl | tert.-butyl | methyl | |
| 9 | pent-3-yl | tert.-butyl | methyl | |
| 10 | 1,2-dimethyl-propyl | tert.-butyl | methyl | |
| 11 | n-hexyl | tert.-butyl | methyl | |
| 12 | hex-2-yl | tert.-butyl | methyl | |
| 13 | hex-3-yl | tert.-butyl | methyl | |
| 14 | 1,2,2-trimethyl-propyl | tert.-butyl | methyl | |
| 15 | 1,3-dimethyl-butyl | tert.-butyl | methyl | |
| 16 | 4-methyl-pentyl | tert.-butyl | methyl | |
| 17 | 3,3-dimethyl-butyl | tert.-butyl | methyl | oil 2955, 2909, 2868, 2800, 1510, 1476, 1465, 1363, 829, 574. |
| 18 | n-heptyl | tert.-butyl | methyl | |
| 19 | hept-2-yl | tert.-butyl | methyl | |
| 20 | hept-3-yl | tert.-butyl | methyl | |
| 21 | hept-4-yl | tert.-butyl | methyl | |
| 22 | diisopropyl-methyl | tert.-butyl | methyl | |
| 23 | 1,4-dimethyl-pentyl | tert.-butyl | methyl | |
| 24 | 4,4-dimethyl-pentyl | tert.-butyl | methyl | bp. 166–170° C./2 mbar |
| 25 | n-octyl | tert.-butyl | methyl | |
| 26 | 2-methyl-hept-3-yl | tert.-butyl | methyl | |
| 27 | 5-methyl-hept-3-yl | tert.-butyl | methyl | |
| 28 | oct-2-yl | tert.-butyl | methyl | |
| 29 | oct-3-yl | tert.-butyl | methyl | |
| 30 | oct-4-yl | tert.-butyl | methyl | |
| 31 | 5,5-dimethyl-hexyl | tert.-butyl | methyl | |
| 32 | 2,4,4-trimethyl-pentyl | tert.-butyl | methyl | oil 2955, 2910, 2868, 1476, 1462, 1375, 1363, 829, 573. |
| 33 | 6-methyl-hept-2-yl | tert.-butyl | methyl | bp. 145° C./0,4 mbar |
| 34 | n-nonyl | tert.-butyl | methyl | |
| 35 | non-2-yl | tert.-butyl | methyl | |
| 36 | non-3-yl | tert.-butyl | methyl | |
| 37 | non-4-yl | tert.-butyl | methyl | |
| 38 | non-5-yl | tert.-butyl | methyl | |
| 39 | 2,5,5-trimethyl-hexyl | tert.-butyl | methyl | |
| 40 | 2,6-dimethyl-hept-4-yl | tert.-butyl | methyl | |
| 41 | 3,5,5-trimethyl-hexyl | tert.-butyl | methyl | Sdp. 170–175° C./2 mbar |
| 42 | n-decyl | tert.-butyl | methyl | |
| 43 | dec-2-yl | tert.-butyl | methyl | |
| 44 | dec-3-yl | tert.-butyl | methyl | |
| 45 | dec-4-yl | tert.-butyl | methyl | |
| 46 | 2,3,5,5-tetramethyl-hexyl | tert.-butyl | methyl | |
| 47 | n-undecyl | tert.-butyl | methyl | |
| 48 | n-dodecyl | tert.-butyl | methyl | |
| 49 | n-tridecyl | tert.-butyl | methyl | |
| 50 | 1,5,9-trimethyl-decyl | tert.-butyl | methyl | |
| 51 | n-tetradecyl | tert.-butyl | methyl | |
| 52 | 2-hydroxyethyl | tert.-butyl | methyl | |
| 53 | 3-hydroxypropyl | tert.-butyl | methyl | |
| 54 | 4-hydroxy-butyl | tert.-butyl | methyl | |
| 55 | 1-hydroxy-but-2-yl | tert.-butyl | methyl | |
| 57 | 2-hydroxy-but-3-yl | tert.-butyl | methyl | |
| 58 | 3-chloropropyl | tert.-butyl | methyl | |
| 59 | 6-chlorohexyl | tert.-butyl | methyl | |
| 60 | trifluoroethyl | tert.-butyl | methyl | |
| 61 | trichloroethyl | tert.-butyl | methyl | |
| 62 | 5-chloropent-2-yl | tert.-butyl | methyl | |
| 63 | 3-chlorobut-2-yl | tert.-butyl | methyl | |
| 64 | 3,3-dichloroprop-2-yl | tert.-butyl | methyl | |
| 65 | 2-methoxyethyl | tert.-butyl | methyl | |
| 66 | 2-ethoxyethyl | tert.-butyl | methyl | |

TABLE 1-continued

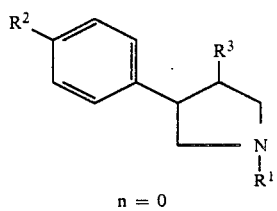

n = 0

| Comp. No. | R¹ | R² | R³ | IR absorption (cm⁻¹) [film] |
|---|---|---|---|---|
| 67 | 2-tert.-butoxyethyl | tert.-butyl | methyl | |
| 68 | 3-tert.-butoxy-ethyl | tert.-butyl | methyl | |
| 69 | 6-methoxyhexyl | tert.-butyl | methyl | |
| 70 | 3-methoxy-prop-2-yl | tert.-butyl | methyl | |
| 71 | trimethylsilylethyl | tert.-butyl | methyl | |
| 72 | 3-trimethylsilyl-propyl | tert.-butyl | methyl | |
| 73 | 6-trimethylsilyl-hexyl | tert.-butyl | methyl | |
| 74 | allyl | tert.-butyl | methyl | |
| 75 | 3-methyl-but-2-en-yl | tert.-butyl | methyl | |
| 76 | 1,5,9-trimethyl-deca-4,8-chenyl | tert.-butyl | metyhl | |
| 77 | propargyl | tert.-butyl | methyl | |
| 78 | 4,4-dimethyl-but-yn-1-yl | tert.-butyl | methyl | |
| 79 | cyclopentyl | tert.-butyl | methyl | |
| 80 | cyclohexyl | tert.-butyl | methyl | oil 2957, 2928, 2854, 2775, 1509, 1462, 1450, 1374, 1363, 829. |
| 81 | cycloheptyl | tert.-butyl | methyl | |
| 82 | 4-hydroxy-cyclohexyl | tert.-butyl | methyl | |
| 83 | 4-tert.-butoxy-cyclohexyl | tert.-butyl | methyl | |
| 84 | 4-trimethylsolyl-cyclohexyl (cis-trans mixture) | tert.-butyl | methyl | |
| 85 | cyclohex-2-en-yl | tert.-butyl | methyl | |
| 86 | 4-methyl-cyclohexyl | tert.-butyl | methyl | |
| 87 | 3-methyl-cyclohexyl | tert.-butyl | methyl | |
| 88 | 3,3-dimethyl-cyclohexyl | tert.-butyl | methyl | oil 2952, 2925, 2865, 2781, 1509, 1475, 1461, 1385, 1363, 1122, 829, 574. |
| 89 | 3,3,5-trimethylcyclohexyl | tert.-butyl | methyl | |
| 90 | 4-isopropyl-cyclohexyl (isomer mixture) | tert.-butyl | methyl | oil 2956, 2934, 2867, 2774, 1509, 1475, 1462, 1450, 1375, 1366, 828, 574. |
| 91 | trans-4-isopropyl-cyclohexyl | tert.-butyl | methyl | |
| 92 | 4-tert.-butyl-cyclohexyl (isomer mixture) | tert.-butyl | methyl | |
| 93 | trans-4-tert.butyl-cyclohexyl | tert.-butyl | methyl | |
| 94 | 4(2-methyl-but-2-yl)cyclohexyl (isomer mixture) | tert.-butyl | methyl | |
| 95 | trans-4(2-methyl-but-2-yl)-cyclohexyl | tert.-butyl | methyl | |
| 96 | 4(2,4,4-trimethyl-pent-2-yl) cyclohexyl (isomer mixture) | tert.-butyl | methyl | |
| 97 | trans-4(2,4,4-trimethyl-pent-2-yl)cyclohexyl | tert.-butyl | methyl | |
| 98 | 4-hydroxy-3-methyl-cyclohexyl | tert.-butyl | methyl | |
| 99 | 4-hydroxy-3,6-dimethyl-cyclohexyl | tert.-butyl | methyl | |
| 100 | 4-hydroxy-3,3-dimethyl-cyclohexyl | tert.-butyl | methyl | |
| 101 | 4-hydroxy-3,3,5-trimethyl-cyclohexyl | tert.-butyl | methyl | resin 3440, 2958, 2928, 2868, 1475, 1460, 1376, 1363, 1333, 829, 575. |
| 102 | cyclohexylmethyl | tert.-butyl | methyl | |
| 103 | cyclohexylethyl | tert.-butyl | methyl | |
| 104 | 4-tert.-buyl-cyclohex-3-en-yl | tert.-butyl | methyl | |
| 105 | 4-tert.-butyl-cyclohex-2-en-yl | tert.-butyl | methyl | |
| 106 | 1-decalyl (cis/trans mixture) | tert.-butyl | methyl | |
| 107 | 2-decalyl (cis/trans mixture) | tert.-butyl | methyl | resin 2956, 2921, 2862, 2776, 1509, 1476, 1459, 1448, 1375, 1362, 829, 575. |
| 108 | trans-2-decalyl (eq/ax.-substituted) | tert.-butyl | methyl | |
| 109 | eq.-trans-2-decalyl | tert.-butyl | methyl | |
| 110 | 6-hydroxy-2-decalyl | tert.-butyl | methyl | |
| 111 | 7-hydroxy-2-decalyl | tert.-butyl | methyl | |
| 112 | 2-decalylmethyl | tert.-butyl | methyl | |
| 113 | 9-methyl-trans-2-decalyl | tert.-butyl | methyl | |
| 114 | 5,9-dimethyl-trans-2-decalyl | tert.-butyl | methyl | |
| 115 | 5,5,9-trimethyl-trans-2-decalyl | tert.-butyl | methyl | |
| 116 | 6-hydroxy-9-methyl-2-decalyl | tert.-butyl | methyl | |
| 117 | 6-hydroxy-5,9-dimethyl-2-decalyl | tert.-butyl | methyl | |
| 118 | 6-hydroxy-5,5,9-trimethyl2-decalyl | tert.-butyl | methyl | |
| 119 | tetrahydropyran-4-yl | tert.-butyl | methyl | oil 2956, 2924, 2867, 2773, 1362, 1174, 1164, 1095, 831. |
| 120 | tetrahydrothiopyran-4-yl | tert.-butyl | methyl | |

TABLE 1-continued

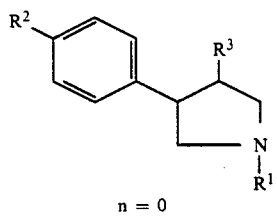

n = 0

| Comp. No. | R¹ | R² | R³ | IR absorption (cm⁻¹) [film] |
|---|---|---|---|---|
| 121 | 1,4-dioxan-2-yl-methyl | tert.-butyl | methyl | bp. 190–200° C./2 mbar |
| 122 | tetrahydropyran-2-yl-methyl | tert.-butyl | methyl | bp. 160–175° C./2 mbar |
| 123 | tetrahydropyran-3-yl-methyl | tert.-butyl | methyl | bp. 156–158° C./2 mbar |
| 124 | 3,5-dimethyl-dioxan-2-yl-methyl | tert.-butyl | methyl | bp. 177–190° C./3 mbar |
| 125 | 3,5-diethyl-dioxan-2-yl-methyl | tert.-butyl | methyl | bp. 168–172° C./3 mbar |
| 126 | 3,6-diethyl-dioxan-2-yl-methyl | tert.-butyl | methyl | bp. 168–172° C./3 mbar |
| 127 | phenyl | tert.-butyl | methyl | |
| 128 | 4-hydroxy-phenyl | tert.-butyl | methyl | |
| 129 | 4-chlorophenyl | tert.-butyl | methyl | |
| 130 | 4-tert.-butoxy-phenyl | tert.-butyl | methyl | |
| 131 | benzyl | tert.-butyl | methyl | bp. 176–180° C./4 mbar |
| 132 | 4-chlorobenzyl | tert.-butyl | methyl | |
| 133 | 2,4-dichlorobenzyl | tert.-butyl | methyl | |
| 134 | 4-tert.-butoxybenzyl | tert.-butyl | methyl | |
| 135 | 4-trimethylsolylbenzyl | tert.-butyl | methyl | |
| 136 | 4-phenyl-4-methyl-pentyl | tert.-butyl | methyl | bp. 220° C./4 mbar |
| 137 | 4-tert.-butylbenzyl | tert.-butyl | methyl | bp. 210° C./4 mbar |
| 138 | 4-tert.-butylphenylethyl | tert.-butyl | methyl | |
| 139 | 4-tert.-butylphenylpropyl | tert.-butyl | methyl | |
| 140 | 3,3-dimethyl-butyl | 2-methyl-but-2-yl | methyl | |
| 141 | 3,5,5-trimethyl-hexyl-cyclohexyl | 2-methyl-but-2-yl | methyl | |
| 142 | 3-methyl-cyclohexyl | 2-methyl-but-2-yl | methyl | |
| 143 | 3,3-dimethyl-cyclohexyl | 2-methyl-but-2-yl | methyl | |
| 144 | 4-isopropyl-cyclohexyl | 2-methyl-but-2-yl | methyl | |
| 145 | 4-tert.-butyl-cyclohexyl (isomer mixture) | 2-methyl-but-2-yl | methyl | |
| 146 | trans-4-tert.-butyl-cyclohexyl | 2-methyl-but-2-yl | methyl | |
| 147 | 4-tert.-butyl-cyclohexyl | 2-methyl-but-2-yl | methyl | |
| 148 | 4-trimethylsilylcyclohexyl | 2-methyl-but-2-yl | methyl | |
| 149 | 4-hydroxy-cyclohexyl | 2-methyl-but-2-yl | methyl | |
| 150 | 3,3,5-trimethyl-cyclohexyl | 2-methyl-but-2-yl | methyl | |
| 151 | 2-decalyl | 2-methyl-but-2-yl | methyl | |
| 152 | 6-hydroxy-2-decalyl | 2-methyl-but-2-yl | methyl | |
| 153 | 5,5,9-trimethyl-2-decalyl | 2-methyl-but-2-yl | methyl | |
| 154 | 6-hydroxy-5,9-dimethyl-2-decalyl | 2-methyl-but-2-yl | methyl | |
| 155 | 6-hydroxy-5,5,9-trimethyl-2-decalyl | 2-methyl-but-2-yl | methyl | |
| 156 | 4-isopropyl-cyclohexyl | 2,4,4-trimethyl-pent-2-yl | methyl | |
| 157 | 3,3-dimethyl-cyclohexyl | 2,4,4-trimethyl-pent-2-yl | methyl | |
| 158 | 3,3-dimethyl-butyl | 2,4,4-trimethyl-pent-2-yl | methyl | |
| 159 | 4-tert.-butyl-cyclohexyl | 2,4,4-trimethyl-pent-2-yl | methyl | |
| 160 | 4-trimethylsilyl-cyclohexyl | 2,4,4-trimethyl-pent-2-yl | methyl | |
| 161 | 2-decalyl | 2,4,4-trimethyl-pent-2-yl | methyl | |
| 162 | 6-hydroxy-2-decalyl | 2,4,4-trimethyl-pent-2-yl | methyl | |
| 163 | 5,5,9-trimethyl-2-decalyl | 2,4,4-trimethyl-pent-2-yl | methyl | |
| 164 | 6-hydroxy-5,9-dimethyl-decalyl | 2,4,4-trimethyl-pent-2-yl | methyl | |
| 165 | 4-tert.-butyl-cyclohexyl | tert.-butoxy | methyl | |
| 166 | 4-trimethylsilyl-cyclohexyl | tert.-butoxy | methyl | |
| 167 | 3,3-dimethyl-butyl | tert.-butoxy | methyl | |
| 168 | 3,3-dimethyl-cyclohexyl | tert.-butoxy | methyl | |
| 169 | 4-hydroxy-3,3,5-trimethyl-cyclohexyl | tert.-butoxy | methyl | |
| 170 | 4-tert.-butyl-cyclohexyl | tert.-butyl | ethyl | |
| 171 | 4-tert.-butyl-cyclohexyl | tert.-butyl | propyl | |
| 172 | 4-tert.-butyl-cyclohexyl | tert.-butyl | butyl | |
| 173 | 3(4-tert.-butyl-phenyl)2-methyl-propyl | tert.-butyl | methyl | bp. 215–220° C./2 mbar |
| 174 | 3,6-dimethyl-dioxan-2-yl-methyl | tert.-butyl | methyl | bp. 177–190° C./3 mbar | eq/ax = substitution in equatorial or axial position

TABLE 2

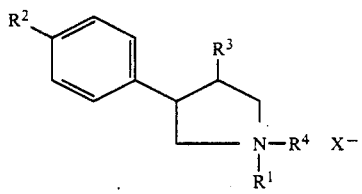

n = 1

| Comp. No. | R¹ | R² | R³ | R⁴ | X⁻ | |
|---|---|---|---|---|---|---|
| 175 | 4-tert.-butyl-cyclohexyl | tert.-butyl | methyl | methyl | I | |
| 176 | 4-tert.-butyl-cyclohexyl | tert.-butyl | methyl | methyl | Cl | |
| 177 | 4-tert.-butyl-cyclohexyl | tert.-butyl | methyl | Ethyl | I | |
| 178 | 2-decalyl | tert.-butyl | methyl | methyl | I | |
| 179 | 2-decalyl | tert.-butyl | methyl | methyl | Cl | |
| 180 | 6-hydroxy-2-decalyl | tert.-butyl | methyl | methyl | I | |
| 181 | 5,5,9-trimethyl-2-decalyl | tert.-butyl | methyl | methyl | I | |
| 182 | 5,5,9-trimethyl-2-decalyl | tert.-butyl | methyl | methyl | Cl | |
| 183 | 6-hydroxy-5,5,9-trimethyl-2-decalyl | tert.-butyl | methyl | methyl | Cl | |
| 184 | 3,3,5-trimethyl-hexyl | tert.-butyl | methyl | methyl | I | mp. 145–175° C. |
| 185 | 3(4-tert.-butylphenyl)-2-methyl-propyl | tert.-butyl | methyl | methyl | I | Mp. 168–185° C. |
| 186 | tetrahydropyran-3-yl-methyl | tert.-butyl | methyl | methyl | I | mp. 180–188° C. |
| 187 | 4-tert.-butyl-benzyl | tert.-butyl | methyl | Alkyl | Br | mp. 105–114° C. |
| 188 | 2,3,5,5-tetramethyl-hexyl | tert.-butyl | methyl | methyl | I | mp. 219–245° C. |
| 189 | 2,3,5,5-tetramethyl-hexyl | tert.-butyl | methyl | methyl | Br | mp. 250–270° C. |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*.

Some of the novel compounds have a very good action on human-pathogenic fungi, such as *Trichophyton mentagrophytes* and *Candida albicans*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 41 is mixed with 10 parts by weight of N-methyl-α-pyrrolidone. A mixture is obtained which is suitable for application in the form of very fine drops.

II. 20 parts by weight of compound no. 121 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 24 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 122 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 123 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 124 is intimately mixed with 97 parts by weight of particulate kaolin. A dust is obtained containing 3% by weight of the active ingredient.

VII. 30 parts by weight of compound no. 131 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 136 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 137 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and
N,N'-polypropylenebis(thiocarbamyl) disulfide;

nitro derivatives, such as dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as 2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide), 1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1yl)-butan-2-one,
1-(4-chlorophenoxy)-3,3-dimethyl-1-(1H-1,2,4triazol-1yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The agent used for comparison purposes was N-2-methyl-3-(p-tert-butyl-phenyl)-propylpyrrolidine (A) disclosed in DE-2,727,482.

Use Example 1

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients, 24, 41, 121, 122, 123, 124, 131, 137, 136, 173, 189, 184, 185 and 188, when applied as 0.05 wt % spray liquors, had a better fungicidal action (97%) than prior art comparative agent A (60%).

Use Example 2

Action on *Botrytis cinerea* in Paprika

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results show that active ingredients 41, 121, 122, 123, 124, 137, 136, 173, 184, 185, 186, 187 and 188, applied as 0.05 wt % spray liquors, had a better fungicidal action (90%) than prior art comparative agent A (50%).

Use Example 3

Action on Barley Mildew

Leaves of pot-grown barley seedlings of the "Igri" variety were sprayed with aqueous liquors containing (dry basis) 80% of active ingredient and 20% of emulsifier, and dusted after 24 hours with spores of barley mildew (*Erysiphe graminis* var. hordei). The plants were then set up in the greenhouse at 20° to 22° C. and a relative humidity of 75 to 80%. The extent of mildew spread was assessed after 7 days.

The results show that active ingredients 24, 41, 121, 122, 123, 124, 131, 185 and 188, applied as 0.006 and 0.0015% spray liquors, had a better fungicidal action (97%) than prior art comparative agent A (70%).

We claim:

1. N-substituted 3-alkyl-4-aryl-pyrrolidine derivatives of the formula

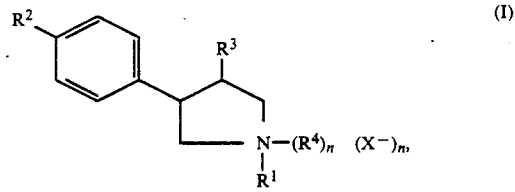

where
R$^1$ is C$_2$-C$_{20}$-alkyl which is unsubstituted or substituted by hydroxy, halogen, C$_1$-C$_5$-alkoxy or C$_3$-C$_9$-trialkylsilyl, C$_3$-C$_{20}$-alkenyl, C$_3$-C$_{20}$-alkynyl, C$_4$-C$_{12}$-cycloalkyl which is unsubstituted or substituted by hydroxy, C$_1$-C$_5$-alkoxy or C$_3$-C$_9$-trialkylsilyl, C$_4$-C$_{12}$-cycloalkenyl, C$_4$-C$_{20}$-alkylcycloalkyl which is unsubstituted or substituted by hydroxy, $C_4$–$C_{20}$-cycloalkyl-alkyl, $C_4$–$C_{20}$-alkyl-cycloalkylalkyl, $C_4$–$C_{20}$-cycloalkenyl-alkyl, $C_4$–$C_{20}$-alkyl-cycloalkenyl, hydroxy-substituted or unsubstituted $C_9$–$C_{11}$-bicycloalkyl, $C_{10}$–$C_{15}$-bicycloalkylalkyl, hydroxy-substituted or unsubstituted $C_{10}$–$C_{15}$-alkylbicycloalkyl, 5 to 7-membered heterocycloalkyl having 1 to 2 heteroatoms selected from the group consisting of oxygen and sulfur, 5 to 7-membered heterocycloalkylmethyl having 1 or 2 heteroatoms selected from the group consisting of oxygen and sulfur, $C_1$–$C_8$-alkyl-substituted 5 to 7-membered heterocycloalkyl or heterocycloalkylmethyl having 1 or 2 heteroatoms selected from the group consisting of oxygen and sulfur, substituted or unsubstituted aryl, substituted or unsubstituted $C_7$–$C_{20}$-arylalkyl, $C_7$–$C_{20}$-alkylaryl, $C_8$–$C_{20}$-alkyl-aryl-alkyl, wherein the aryl substituents are selected from the group consisting of hydroxy, halo, $C_1$–$C_5$-alkoxy and $C_3$–$C_9$-trialkylsilyl, $R^2$ is $C_{3-C_8}$-alkoxy,
$R^3$ is $C_1$–$C_4$-alkyl,
$R^4$ is $C_1$–$C_5$-alkyl, $C_3$–$C_5$-alkenyl, $C_3$–$C_5$-alkynyl or $C_7$–$C_8$-phenylalkyl,
$X^-$ is a plant-tolerated anion,
n is 0 or 1,
or a plant-tolerated salt thereof.

2. A fungicidal composition containing an inert carrier and a fungicidally effective amount a compound of claim 1.

3. A process for combating fungi, wherein the fungi or the materials, plants, seed or soil to be protected against fungus attack are treated with a compound of claim 1.

4. N-substituted 3-alkyl-4-aryl-pyrrolidine derivatives of the formula

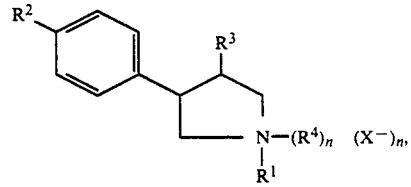

where
$R^1$ $C_2$–$C_{20}$-alkyl which is substituted by halogen or $C_3$–$C_9$-trialkylsilyl, 5 to 7-membered heterocycloalkyl having 1 to 2 heteroatoms selected from the group consisting of oxygen and sulfur, 5 to 7-membered heterocycloalkylmethyl having 1 to 2 heteroatoms which are sulfur, $C_1$–$C_8$-alkyl-substituted 5 to 7-membered heterocycloalkyl having 1 or 2 heteroatoms selected from the group consisting of oxygen and sulfur, or $C_1$–$C_8$-alkyl-substituted 5 to 7-membered heterocycloalkylmethyl having 1 or 2 heteroatoms which are sulfur, $R^2$ is $C_3$–$C_{10}$-alkyl, or $C_3$–$C_8$-alkoxy,
$R^3$ is $C_1$–$C_4$-alkyl,
$R^4$ is $C_1$–$C_5$-alkyl, $C_3$–$C_5$-alkenyl, $C_3$–$C_5$-alkynyl or $C_7$–$C_8$-phenylalkyl,
$X^-$ is a plant-tolerated anion,
n is 0 or 1,
or a plant-tolerated salt thereof.

5. A fungicidal composition containing an inert carrier and a fungicidally effective amount of a compound of claim 4.

6. A process for combating fungi, wherein the fungi or the materials, plants, seed or soil to be protected against fungus attack are treated with a compound of claim 4.

* * * * *